United States Patent [19]

Grasselli et al.

[11] 4,271,091

[45] Jun. 2, 1981

[54] VAPOR PHASE CATALYTIC OXIDATION AND/OR AMMOXIDATION OF CYCLOHEXANONE AND/OR CYCLOHEXANOL TO PHENOL AND/OR ANILINE

[75] Inventors: Robert K. Grasselli, Chagrin Falls; Dev D. Suresh, Macedonia, both of Ohio

[73] Assignee: Standard Oil Company, Cleveland, Ohio

[21] Appl. No.: 916,649

[22] Filed: Jun. 17, 1978

[51] Int. Cl.$^3$ .................. C07C 85/06; C07C 7/144; C07C 7/12
[52] U.S. Cl. .................. 564/305; 568/799; 568/802; 568/771; 568/772; 568/807; 568/814; 568/815; 568/816; 568/819; 568/821; 568/838; 568/839
[58] Field of Search .............. 252/461, 467; 260/581; 568/799, 838

[56] References Cited

U.S. PATENT DOCUMENTS

| | | | |
|---|---|---|---|
| 3,347,921 | 10/1967 | Carrubba et al. | 260/581 X |
| 3,534,110 | 10/1970 | Juguin et al. | 568/799 |
| 3,553,268 | 1/1971 | Solomon et al. | 260/581 |
| 3,850,995 | 11/1974 | Horlenko et al. | 568/802 |
| 3,885,020 | 5/1975 | Whelan | 568/802 X |
| 3,985,680 | 10/1976 | Allen | 252/467 X |
| 4,059,628 | 11/1977 | De Pesco et al. | 260/581 |

FOREIGN PATENT DOCUMENTS

| | | | |
|---|---|---|---|
| 453546 | 12/1948 | Canada | 260/581 |
| 1144731 | 3/1963 | Fed. Rep. of Germany | 568/799 |
| 40-4741 | 3/1965 | Japan | 568/799 |
| 986932 | 3/1965 | United Kingdom | 568/799 |

OTHER PUBLICATIONS

Kosower et al., "J. Org. Chem.", vol. 28, pp. 633-638 (1963).
Manninger et al., "Heterogeneous Catalytic Reactions of Cyclohexanol . . . ", in Chem. Abs. 85:108127r, 1976.
Skrigan, "Dehydrogenation of the Cyclohexanol-Cyclohexanone Mixture to Phenol", in Chem. Abs. 84:30575t, 1976.
Richardson, J. et al., "Dehydrogenation and Amination of Cyclohexanol by Pt. Catalysts", in Chem. Abs. 1976, 85:93377w.
Bauger, L. et al., "Aliphatic Dinitrites", in Chem. Abs. 80745a, vol. 71, 1969.

*Primary Examiner*—John Doll
*Attorney, Agent, or Firm*—John E. Miller, Jr.; Herbert D. Knudsen; Larry W. Evans

[57] ABSTRACT

Cyclohexanone and/or cyclohexanol can be oxidized in the vapor phase to phenol by contacting the cyclohexanone and/or cyclohexanol with a suitable oxidation catalyst in the presence of molecular oxygen. Suitable catalysts are solids comprising Mo, W, Sb and/or V oxides or complexes thereof. The catalysts may be promoted with additional elements.

19 Claims, No Drawings

VAPOR PHASE CATALYTIC OXIDATION AND/OR AMMOXIDATION OF CYCLOHEXANONE AND/OR CYCLOHEXANOL TO PHENOL AND/OR ANILINE

BACKGROUND OF THE INVENTION

The present invention relates to a catalytic process for oxidizing cyclohexanone and/or cyclohexanol to form phenol.

Processes for producing phenol from cyclohexanone and/or cyclohexanol catalytically are known. See, for example, U.S. Pat. No. 3,580,970 which discloses a catalytic process of this type, the process using a metallic catalyst and being carried out under reducing conditions.

Although such processes are capable of forming phenol from cyclohexanone and/or cyclohexanol, they suffer various disadvantages due to the fact that the process is carried out under reducing conditions and the catalyst is metallic.

Accordingly, it is an object of the present invention to provide a new process for catalytically forming phenol from cyclohexanone and/or cyclohexanol which need not be carried out under reducing conditions and which may use a catalyst other than a free metal.

SUMMARY OF THE INVENTION

This and other objects are accomplished by the present invention in accordance with which cyclohexanone and/or cyclohexanol in the presence of molecular oxygen is contacted in the vapor phase with a suitable oxidation catalyst. The oxidation catalysts useful in accordance with the present invention are solids which contain oxides of Mo, W, Sb, and/or V, or complexes thereof, which may optionally and preferably be promoted with additional elements. In accordance with the present invention, it has been found that phenol can be produced in significant yields by this procedure, thereby making the instant invention of significant commercial interest.

In accordance with another aspect of the present invention, it has been further found that aniline can be obtained as a useful product in the inventive process by the expedient of adding a suitable amount of ammonia to the reaction system.

Thus, the present invention provides a novel process comprising contacting a cycloaliphatic ketone or alcohol in which the oxygen atom is directly connected to a ring carbon atom, or mixtures thereof, and molecular oxygen with an oxidation catalyst comprising an oxide or oxide complex containing Mo, W, Sb, V or mixtures thereof.

DETAILED DESCRIPTION

The present invention is primarily directed to producing phenol from cyclohexanone and/or cyclohexanol. However, other cycloaliphatic ketones and alcohols can be processed in accordance with the present invention to dehydrogenate the cycloaliphatic rings thereof. Thus, the starting material of the inventive process can be any cycloaliphatic ketone or alcohol wherein the oxygen is directly connected to a ring carbon atom. By cycloaliphatic is meant a ring-type compound which is at least partially saturated, and may be mononuclear or polynuclear, that is containing from one to four rings, in which the ring to which the oxygen atom is attached is at least partially saturated. These cycloaliphatic ketones and alcohols include those compounds which contain from one to three oxygen atoms each of which is directly connected to a ring carbon atom. The preferred cycloaliphatic compounds are the mononuclear naphthenic type compounds of the general formula $C_nH_{2n}$, wherein n is the integer 5 or 6. The especially preferred charge stock is cyclohexanone, cyclohexanol, and mixtures of the two. The ring compounds can have one or more groups attached to the ring which do not interfere with the ammoxidation reaction, such as lower alkyl having from one to four carbon atoms, phenyl, benzyl, tolyl, xylyl, etc. The charge stock compounds can suitably contain between 4 and 18 carbon atoms per molecule and preferably contain between 6 and 10 carbon atoms. Suitable charge stock compounds include the following without being limited, thereto, cyclohexanol,
cyclohexanone,
cyclohexanol,
cyclohexanone,
1,3-cyclohexanediol,
1,4-cyclohexanediol,
1,3-cyclohexanedione,
1,4-cyclohexanedione,
4-methylcyclohexanone,
4-t, butylcyclohexanol,
3,5-dimethylcyclohexanone,
4-phenylcyclohexanone,
3-tolycyclohexanone,
cyclopentanone,
3-methylcyclopentanol,
2-ketotetralin,
2-(1-cyclohexenyl)cyclohexanone,
2,6-dicyclohexenylcyclohexanone, etc.

Of course, when cyclopentanol and/or cyclopentanone or derivates thereof are employed as the feed, the terminal aliphatic rings on the reaction product will have 5 members, not 6.

In the embodiment of the invention in which aniline is a desired product, the feed may also contain cyclohexylamine. Indeed, the feed can be composed entirely of cyclohexylamine since this material results in very high yields of aniline.

The inventive reaction is carried out in the presence of molecular oxygen. The oxygen may be supplied in the form of pure $O_2$, or it may be supplied in the form of air or any other mixture of $O_2$ and an inert diluent. Air is the preferred source of $O_2$ since it is cheapest and most readily available. The molecular oxygen may be fed to the reactors separately or already admixed with the charge stock.

The amount of molecular oxygen fed to the reactor can vary between wide limits. It should be above the stoichiometric amount, although this is not essential, and should not be so much that the reactor becomes uneconomically large. Preferably, the amount of oxygen fed to the reactor is such that the ratio of the amount of oxygen to the amount of ketone and/or alcohol in the charge stock is 0.1–20 to 1, most preferably 0.5–3 to 1.

In addition to molecular oxygen, an inert diluent may also be fed to the reactor. Inert diluents aid in controlling the reaction temperature and serve other useful functions as well known by those skilled in the art. Any material which is inert and gaseous at the reaction temperature can be used as the diluent. Examples of materials found to be especially useful as diluents are steam, carbon dioxide, nitrogen and the like.

In the embodiment of the invention in which aniline is a desired product, the reaction system also contains ammonia. The ammonia can be fed to the reactor separately or together with one or more of the other reactants. The amount of ammonia in the reaction system should be such that the ratio of the amount of ammonia to the amount of ketone and/or alcohol is 0.1-10 to 1, most preferably 1-3 to 1.

The reaction is carried out at an elevated temperature, normally 250° C. to 600° C. Preferably, however, the reaction temperature is maintained between 300° to 550° C., most preferably 350° to 500° C. The reaction pressure can be atmospheric, subatmospheric and superatmospheric.

The inventive reaction is carried out in the vapor phase, either in fixed-bed or fluid-bed mode. The size and configuration of the catalysts are conventional and are determined, of course, depending upon the mode of reaction.

The catalyst useful in the inventive process can be selected from a wide variety of known oxidation catalysts. These catalysts can be described generically as solids which contain one or more oxides of Mo, W, Sb and V, or oxide complexes thereof. Preferred catalysts contain at least one of these four elements but are generally further refined by the addition of other elements as promoters. Catalysts of this type are generally believed in the art to be complex molybdates, tungstates, antimonates and vanadates.

Molybdate catalysts which are useful in the present invention can be generically described by the formula $$A_a B_b C_c D_d Mo_e O_x$$

wherein
 A is Cu, Fe, Ni, Co, Mn, U, Ce, Th, Ag or mixtures thereof;
 B is V, P, Nb, Sb, As, B, Sn or mixtures thereof;
 C is W, Cr or mixtures thereof;
 D is alkali metal; earth alkali, Group IIB, Tl or mixtures thereof; and
wherein
 a is 0 to 6;
 b is 0.01 to 12;
 c is 0 to 12;
 d is 0 to 4;
 e is 6 to 18; and
 x is a number determined by the valence requirements of the other elements present.

Specific examples of such catalysts are:
$V_3W_{1.2}Mo_{12}O_x$
$P_1Mo_{12}O_x$
$Bi_9PMo_{12}O_x$
$K_{0.1}Ni_{2.5}Co_{0.5}Fe_3BiP_{0.5}Mo_{12}O_x$
$Sb_2Mo_3O_x \cdot Mo°_{0.06}$
$Co_{4.5}Fe_{4.5}SbMo_{12}O_x$
$Cu_{0.1-3}Sn_{0.5}V_3W_{1.2}Mo_{12}O_x$
$Fe_{0.1-4}Cu_{0-2}V_3Cr_{1.2}Mo_{12}O_x$
$P_1Mo_{8-18}$ Another subgenus of molybdate catalysts useful in the present invention can be described by the following generic formula $$A_a B_b C_c D_d E_e F_f Mo_g O_x$$

wherein
 A is alkali metal, Tl, Sm or mixtures thereof;
 B is Ni, Co, Mn, Mg, other earth alkaline, Group IIB elements, such as Zn or Cd;
 C is Fe, Cr, Ce or mixtures thereof;
 D is Bi or Te;
 E is P, As, B, Sb, W or mixtures thereof;
 F is Ge, Sn, Al, Ag, Au, Pb, Group VIII elements, U, Tl, In, Ta, rare earth metals or mixtures thereof; and
wherein
 a is 0-4;
 b is 0-20;
 c is 0-20;
 d is 0-20;
 e is 0-5;
 f id 0-10;
 g is 6 to 18; and
 x is a number determined by the valence requiements of the other elements present.

Specific examples of these catalysts are:
$MoO_x$
$Bi_aMo_bO_x$: (a,b=0.1-12)
$Fe_aBi_bMo_{12}O_x$: (a,b=0.01-20)
$Cr_aBi_bMo_{12}O_x$: (a,b=0.01-20)
$KFe_aCr_bW_cBi_dMo_{12}O_x$: (a,b,c=0.01-20)
$Fe_aTe_bMo_{12}O_x$: (a,b=0.01-20)

The tungstate type catalysts useful in accordance with the present invention can be selected from a wide variety of known tungstate oxidation catalysts. These catalysts can be described by the same generic formula used above in connection with the molybdate catalyst, the only difference being that tungsten is substituted for molybdenum in the above formulae (and if tungsten appears in the above formulae, it is correspondingly replaced by molybdenum). A particularly useful tungstate catalyst has the following formula:

$$Bi_a W_b O_x$$

wherein
 a is 0.1-12;
 b is 0.1-12; and
 x is a number determined by the valence requirements of the other elements present.

Vanadate catalysts useful in accordance with the present invention can also be selected from a wide variety of known vanadate oxidation catalysts. These materials can also be described by the generic formlae given above in connection with molybdate type catalysts, the only difference being that vanadium is substituted for the molybdenum in the formulas (and if vanadium is present in the formula, it is correspondingly substituted by molybdenum). An example of a vanadate catalyst finding special use in the inventive process is given by the formula $$Li_a Pb_b V_c O_x$$

wherein
 a is 0-2;
 b and c are 0.01-12; and
 x is a number determined by the valence requirements of the other elements present.

The antimonate catalysts useful in the inventive process can also be selected from a wide variety of known antimonate oxidation catalysts. Basically, these catalysts are oxide complexes containing antimony and uranium;

iron and antimony; or iron, uranium and antimony. These catalysts are described in a number of different patents, such as U.S. Pat. Nos. 3,197,419, 3,198,750, 3,338,952 and 3,431,292. These catalysts can be promoted with many different promoters such as tin, manganese, cerium, thorium, vanadium, cobalt, nickel, molybdenum, tungsten, iron, and mixtures thereof. Combinations found especially useful are SnSb oxide, FeSb oxide, MnSb oxide, CeSb oxide, ThSb oxide, VSb oxide, CoSb oxide, NiSb oxide and mixtures thereof.

The catalyst employed in the inventive process may be used either in unsupported form or supported on a carrier. Any inert material known to be useful as a carrier in an oxidation reaction can be employed in the inventive process. Examples of useful carriers are $SiO_2$, $Al_2O_3$, $TiO_2$, $BPO_4$, $SbPO_4$, $ZrO_2$, Alundum balls and the like. The active catalyst material can be incorporated onto or into the carrier in any known technique. For example, the active catalyst material can be coated on the surfaces of the carrier, the active catalytic material can be impregnated into the carrier or the catalyst can be composed of discreet catalyst particles made up of a mixture of the active catalytic material and the carrier.

The reaction product passing out of the reactor contains the desired end product, phenol and/or aniline, as well as various small amounts of adiponitrile and in some occasions ther are condensation products of the reactants and/or reaction intermediates. Such by-products, which are generally heterocyclic 3-ring compounds can be easily converted to the desired end products aniline and/or phenol or to the starting materials by pyrolitic and/or oxydehydrogenation procedures. The reaction product can be separated into its component parts by conventional techniques such as, for example, distillation after condensation.

The objective products of the inventive process, phenol and/or aniline, enjoy wide utility in commerce and are used, inter alia, as solvents and as starting materials for a wide variety of different chemicals such as rubber accelerators, antioxidants, dyes, photographic chemicals, isocyanates for urethane foams, pharmaceuticals and so forth.

SPECIFIC EMBODIMENTS

In order to more thoroughly describe the present invention, the following examples are presented:

EXAMPLE 1

4 cc. of a catalyst comprising 62% $V_3W_{1.2}Mo_{12}O_x$-38% $SiO_2$ was charged into a fixed-bed reactor. A feed composed of 1 cyclohexanone/10 air/10 $H_2O$ at 450° C. was fed over the catalyst with a contact time of 1.0 seconds. Phenol was obtained with a single pass yield of 22.7%.

For the purposes of this application, single pass yield is defined as (Moles Product Obtained)/(Moles Reactant Fed)

EXAMPLE 2

Example 1 was repeated except that the contact time was changed to 0.25 seconds. A single pass yield to phenol of 16.1% was obtained.

EXAMPLE 3

Examples 1 and 2 were repeated using cyclohexanol as the feed. The results obtained were similar to the results obtained in Examples 1 and 2.

EXAMPLE 4

4 cc. of a catalyst comprising 80% $K_{0.1}Ni_{2.5}$-$Co_{4.5}Fe_3$-$BiP_{0.5}Mo_1O_x$-20% $SiO_2$ was charged into a fixed-bed reactor. A feed comprising 1 cyclohexanone/2.5 $NH_3$/10 air/10 $H_2O$ at 450° C. was fed over the catalyst with a 1 second contact time. Aniline, phenol and adiponitrile were obtained with the single pass yield to aniline being 3.1%, the single pass yield to phenol being 11.6% and the single pass yield to adiponitrile being only trace.

EXAMPLES 5–9

Example 4 was repeated except that different catalysts as described in the following Table I were employed. The results obtained are also set forth in the following Table I.

TABLE I

| Ex. | Catalyst | Single Pass Yield | | |
|---|---|---|---|---|
| | | Aniline | Phenol | Adiponitrile |
| 4 | $K_{0.1}Ni_{2.5}Co_{4.5}Fe_3BiP_{0.5}$-$Mo_{12}O_x$-20% $SiO_2$ | 3.1 | 11.6 | Trace |
| 5 | $V_3W_{1.2}Mo_{12}O_x$-38% $SiO_2$ | 10.2 | 19.2 | 0.6 |
| 6 | $P_1Mo_{12}O_x$-20% $SiO_2$ | 8.9 | 10.0 | — |
| 7 | $WO_3$-20% $SiO_2$ | 5.4 | 7.8 | — |
| 8 | $Fe_{0.1}V_1Sb_{4.6}O_x$-40% $SiO_2$ | 0.1 | 18.9 | 0.3 |
| 9 | $Sb_2Mo_3O_x \cdot MO_{0.06}{}^o$ | — | 3.4 | — |

EXAMPLE 10

Examples 4–9 were repeated using cyclohexanol rather than cyclohexanone as the feed. The results obtained are similar to the results obtained in Examples 4–9.

From the foregoing, it will be noted that the present invention provides a novel technique for forming phenol and/or aniline from cyclohexanone. This technique is simple and straightforward to carry out and hence it is of significant commercial interest.

Although only a few embodiments of the present invention have been described above, many modifications can be made without departing from the spirit and scope of the invention. All such modifications are intended to be included within the scope of the present invention, which is to be limited only by the following claims:

We claim:

1. A process comprising contacting a cycloaliphatic ketone or alcohol in which the oxygen atom is directly connected to a ring carbon atom, or mixtures thereof, and molecular oxygen with an oxidation catalyst comprising an oxide or oxide complex containing Mo, W, Sb, V or mixtures thereof in a reaction zone, the amount of oxygen fed to said reaction zone being such that the ratio of the amount of oxygen to the amount of said ketone or alcohol is 0.1/1 to 20/1 on a molar basis.

2. The process of claim 1 wherein ammonia is also contacted with said catalyst and wherein said aliphatic ketone or alcohol is cyclohexanone or cyclohexanol whereby aniline is also produced as a reaction product.

3. The process of claim 2 wherein said ketone, alcohol or mixture thereof is cyclohexanone, cyclohexanol or mixture thereof.

4. The process of claim 3 wherein said catalyst is a molybdate described by the following general formula $$A_aB_bC_cD_dMo_eO_x$$

wherein
A is Cu, Fe, Ni, Co, Mn, U, Ce, Th, Ag or mixtures thereof;
B is V, P, Nb, Sb, As, B, Sn or mixtures thereof;
C is W, Cr or mixtures thereof;
D is alkali metal, earth alkali, Group IIB, Tl or mixtures thereof; and
and wherein
a is 0 to 6;
b is 0.01 to 12;
c is 0 to 12;
d is 0 to 4;
e is 6 to 18; and
x is a number determined by the valence requirements of the other elements present.

5. The process of claim 3 wherein said catalyst is a molybdate of the following general formula $$A_aB_bC_cD_dE_eF_fMo_gO_x$$

wherein
A is alkali metal, Tl, Sm or mixtures thereof;
B is Ni, Co, Mn, Mg, other earth alkaline, Group IIB elements, such as Zn or Cd;
C is Fe, Cr, Ce or mixtures thereof;
D is Bi or Te;
E is P, As, B, Sb, W or mixtures thereof;
F is Ge, Sn, Al, Ag, Au, Pb, Group VIII elements, V, Tl, In, Ta, rare earth metals or mixtures thereof; and
wherein
a is 0–4;
b is 0–20;
c is 0–20;
d is 0–20;
e is 0–5;
f is 0–10;
g is 6 to 18; and
x is a number determined by the valence requirements of the other elements present.

6. The process of claim 3 wherein said catalyst is a tungstate of the following general formula $$A_aB_bC_cD_dW_eO_x$$

wherein
A is Cu, Fe, Ni, Co, Mn, U, Ce, Th, Ag or mixtures thereof;
B is V, P, Nb, Sb, As, B, Sn or mixtures thereof;
C is Mo, Cr or mixtures thereof;
D is alkali metal, earth alkali, Group IIB, Tl or mixtures thereof; and
and wherein
a is 0 to 6;
b is 0.01 to 12;
c is 0 to 12;
d is 0 to 4;
e is 6 to 18; and
x is a number determined by the valence requirements of the other elements present.

7. The process of claim 3 wherein said catalyst is a tungstate of the following general formula $$A_aB_bC_cD_dE_eF_fW_gO_x$$

wherein
A is alkali metal, Tl, Sm or mixtures thereof;
B is Ni, Co, Mn, Mg, other earth alkaline, Group IIB elements, such as Zn or Cd;
C is Fe, Cr, Ce or mixtures thereof;
D is Bi or Te;
E is P, As, B, Sb, Mo or mixtures thereof;
F is Ge, Sn, Al, Ag, Au, Pb, Group VIII elements, U, Tl, In, Ta, rare earth metals or mixtures thereof; and
wherein
a is 0–4;
b is 0–20;
c is 0–20;
d is 0–20;
e is 0–5;
f is 0–10;
g is 6 to 18; and
x is a number determined by the valence requirements of the other elements present.

8. The process of claim 3 wherein said catalyst is a vanadate of the following general formula $$A_aB_bC_cD_dV_eO_x$$

wherein
A is Cu, Fe, Ni, Co, Mn, U, Ce, Th, Ag or mixtures thereof;
B is Mo, P, Nb, Sb, As, B, Sn or mixtures thereof;
C is W, Cr or mixtures thereof;
D is alkali metal, earth alkali, Group IIB, Tl or mixtures thereof; and
wherein
a is 0 to 6;
b is 0.01 to 12;
c is 0 to 12;
d is 0 to 4;
e is 6 to 18; and
x is a number determined by the valence requirements of the other elements present.

9. The process of claim 3 wherein said catalyst is a vanadate of the following general formula $$A_aB_bC_cD_dE_eF_fV_gO_x$$

wherein
A is alkali metal, Tl, Sm or mixtures thereof;
B is Ni, Co, Mn, Mg, other earth alkaline, Group IIB elements, such as Zn or Cd;
C is Fe, Cr, Ce or mixtures thereof;
D is Bi or Te;
E is P, As, B, Sb, W or mixtures thereof;
F is Ge, Sn, Al, Ag, Au, Pb, Group VIII elements, V, Tl, In, Ta, rare earth metals or mixtures thereof; and
wherein
a is 0–4;
b is 0–20;
c is 0–20;
d is 0–20;
e is 0–5;
f is 0–10;
g is 6 to 18; and
x is a number determined by the valence requirements of the other elements present.

10. The process of claim 3 wherein said catalyst is an antimonate, said antimonate further containing at least one of U and Fe.

11. The process of claim 1 wherein the reaction system is free of ammonia.

12. The process of claim 11 wherein said ketone, alcohol or mixture thereof is cyclohexanone, cyclohexanol or mixture thereof.

13. The process of claim 12 wherein said catalyst is a molybdate described by the following general formula

wherein
- A is Cu, Fe, Ni, Co, Mn, U, Ce, Th, Ag or mixtures thereof;
- B is V, P, Nb, Sb, As, B, Sn or mixtures thereof;
- C is W, Cr or mixtures thereof;
- D is alkali metal, earth alkali, Group IIB, Tl or mixtures thereof; and wherein
- a is 0 to 6;
- b is 0.01 to 12;
- c is 0 to 12;
- d is 0 to 4;
- e is 6 to 18; and
- x is a number determined by the valence requirements of the other elements present.

14. The process of claim 12 wherein said catalyst is a molybdate of the following general formula

wherein
- A is alkali metal, Tl, Sm or mixtures thereof;
- B is Ni, Co, Mn, Mg, other earth alkaline, Group IIB elements, such as Zn or Cd;
- C is Fe, Cr, Ce or mixtures thereof;
- D is Bi or Te;
- E is P, As, B, Sb, W or mixtures thereof;
- F is Ge, Sn, Al, Ag, Au, Pb, Group VIII elements, V, Tl, In, Ta, rare earth metals or mixtures thereof; and wherein
- a is 0–4;
- b is 0–20;
- c is 0–20;
- d is 0–20;
- e is 0–5;
- f is 0–10;
- g is 6 to 18; and
- x is a number determined by the valence requirements of the other elements present.

15. The process of claim 12 wherein said catalyst is a tungstate of the following general formula

wherein
- A is Cu, Fe, Ni, Co, Mn, U, Ce, Th, Ag or mixtures thereof;
- B is V, P, Nb, Sb, As, B, Sn or mixtures thereof;
- C is Mo, Cr or mixtures thereof;
- D is alkali metal, earth alkali, Group IIB, Tl or mixtures thereof; and wherein
- a is 0 to 6;
- b is 0.01 to 12;
- c is 0 to 12;
- d is 0 to 4;
- e is 6 to 18; and
- x is a number determined by the valence requirements of the other elements present.

16. The process of claim 12 wherein said catalyst is a tungstate of the following general formula

wherein
- A is alkali metal, Tl, Sm or mixtures thereof;
- B is Ni, Co, Mn, Mg, other earth alkaline, Group IIB elements, such as Zn or Cd;
- C is Fe, Cr, Ce or mixtures thereof;
- D is Bi or Te;
- E is P, As, B, Sb, Mo or mixtures thereof;
- F is Ge, Sn, Al, Ag, Au, Pb, Group VIII elements, U, Tl, In, Ta, rare earth metals or mixtures thereof; and wherein
- a is 0–4;
- b is 0–20;
- c is 0–20;
- d is 0–20;
- e is 0–5;
- f is 0–10;
- g is 6 to 18; and
- x is a number determined by the valence requirements of the other elements present.

17. The process of claim 12 wherein said catalyst is a vanadate of the following general formula

wherein
- A is Cu, Fe, Ni, Co, Mn, U, Ce, Th, Ag or mixtures thereof;
- B is Mo, P, Nb, Sb, As, B, Sn or mixtures thereof;
- C is W, Cr or mixtures thereof;
- D is alkali metal, earth alkali, Group IIB, Tl or mixtures thereof; and wherein
- a is 0 to 6;
- b is 0.01 to 12;
- c is 0 to 12;
- d is 0 to 4;
- e is 6 to 18; and
- x is a number determined by the valence requirements of the other elements present.

18. The process of claim 12 wherein said catalyst is a vanadate of the following general formula

wherein
- A is alkali metal, Tl, Sm or mixtures thereof;
- B is Ni, Co, Mn, Mg, other earth alkaline, Group IIB elements, such as Zn or Cd;
- C is Fe, Cr, Ce or mixtures thereof;
- D is Bi or Te;
- E is P, As, B, Sb, W or mixtures thereof;
- F is Ge, Sn, Al, Ag, Au, Pb, Group VIII elements, V, Tl, In, Ta, rare earth metals or mixtures thereof; and wherein
- a is 0–4;
- b is 0–20;

c is 0–20;
d is 0–20;
e is 0–5;
f is 0–10;
g is 6 to 18; and x is a number determined by the valence requirements of the other elements present.

19. The process of claim 12 wherein said catalyst in an antimonate, said antimonate further containing at least one of U and Fe.

* * * * *